Dec. 12, 1950 E. G. FISHER Plant Pat. 999
ROSE PLANT
Filed Dec. 29, 1949
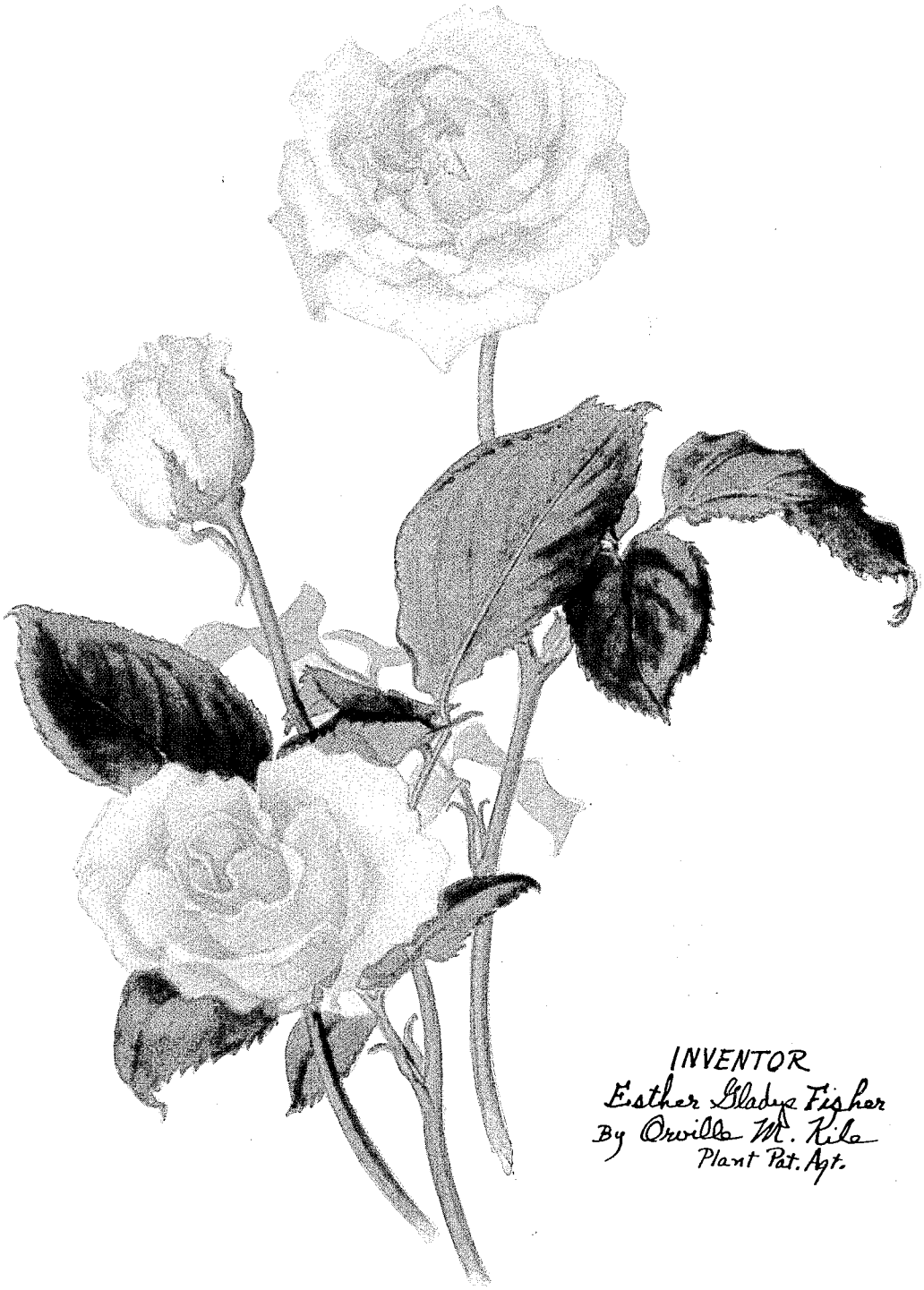
INVENTOR
Esther Gladys Fisher
By Orville M. Kile
Plant Pat. Agt.

Patented Dec. 12, 1950 Plant Pat. 999

UNITED STATES PATENT OFFICE

999

ROSE PLANT

Esther Gladys Fisher, Woburn, Mass., assignor to
Arnold-Fisher Company, Woburn, Mass.

Application December 29, 1949, Serial No. 135,660

1 Claim. (Cl. 47—61)

My present invention relates to a new and distinct variety of hybrid tea rose plant of the novelty type, its flower color being unique in roses.

This variety originated as a self-pollinated seedling from one of my own unnamed seedlings developed in our greenhouses at Woburn, Mass. It has been asexually reproduced at the same place by budding, and its distinguishing features appear to be permanent.

This variety is essentially a greenhouse rose but it can also be grown out-of-doors satisfactorily. It is a prolific producer of flowers and although not a robust grower is adequately strong to produce good bushes. It is not quite so hardy as the really strong growers.

The illustrations accompanying these specifications show a typical flower in three stages of opening as it appeared in the late summer. These illustrations are made as nearly in their true colors as the artist could make them. But it must be borne in mind that the flower varies with the seasons—both as to coloring and to form—although in general it follows those given.

In the following detailed description, color plate numbers rerer to Ridgway's Color Standards and Nomenclature. Other color terminology indicates the ordinary dictionary meaning of the term.

*The plant*

Growth: Medium strength and height. Not a robust grower but adequate for production of a good plant.

Type: Greenhouse variety, but can satisfactorily be grown as a garden rose.

Blooming habit: Constant and prolific producer of blooms throughout the year.

Stem: Slender and wiry. Holds up well. Bright, light green color not found in Ridgway's Color Standards but the nearest is Rinneman's Green (Plate XVIII). Very few thorns are present on the stems and they are small and very light green.

Foliage: 3 to 5 leaflets.

*Quantity.*—Medium, with the terminal leaflet much larger than lateral ones. Terminal leaflet averages about 2½ inches by 1½ inches, while lateral leaflets nearest to it are 1½ inches by 1 inch.

*Color.*—Most of the leaves have a slightly mottled effect due to the fact that the network of veins is darker than the intravenous portions. Veins are approximately Forest Green (Plate XVII) or slightly darker, and the background color is slightly lighter.

*Shape.*—Long oval, with rounded base and acuminate apex.

*Texture.*—Smooth and velvety, without gloss. Rib prominent.

*Edge.*—Finely and sharply serrated.

*Rachis.*—Slender; relatively smooth, with only one or two small spines on under side.

*Stipules.*—Small; clinging, but with long points.

*The flower*

Bud:

*Size.*—Small to medium—about 1 inch long just before unfolding.

*Form.*—Blunt and somewhat ovoid.

Color: Approximately Purplish Lilac (Plate XXXVII).

Sepals: Simple; reflex when bud expands; later clasp stem.

Calyx: Small; smooth.

Peduncle: Short—2 to 3 inches; same color as stem; slender and wiry but strong, holding flower erect.

Opening: Slow. Not affected by adverse weather conditions.

Bloom:

*Borne.*—Singly.

*Size.*—Small to medium, measuring up to 3½ inches across when fully expanded.

*Form.*—High centered; in cool weather opens into deep cupshape with open center and fluted or undulate petals all of good size leaving the center open. In warmer weather the inner petals are usually smaller and tend to cover the center.

*Petalage.*—15 to 20 petals in the average flower.

*Color.*—The color is largely lavender but also contains tones of gray and blue. As the flower begins to open, the predominant color is between Purplish Lilac (Plate XXXVII) and Argyle Purple (same plate). A little later on it becomes lighter in tone, with more gray apparent.

*Scent.*—Pleasing, delicate fragrance.

*Petal texture.*—Soft and silky.

*Longevity.*—Flower lasts very well when cut.

Reproductive organs:

*Pistils.*—Bunched in center of hard pithy round platform, having a tassel-like appearance. *Styles* yellow, uneven lengths. *Stigmas* light orange.

*Stamens.*—Grouped around pistils at outer edge of pithy platform. *Filaments* light cream; uneven lengths; long and curved. *Anthers* large and bright orange, later orange, later turning to brown.

Having thus disclosed my invention, I claim: The new and distinct variety of hybrid tea rose plant, substantially as herein shown and described, characterized particularly by the delicate though strong structure of the stems; its continuous production of flowers throughout the year; the prominent veining of its foliage; the high-centered form of the flower which in the cool season usually opens to cupshape with fluted petals; and the essentially lavender color of its bud and flower.

ESTHER GLADYS FISHER.

No references cited.